US008913804B2

(12) United States Patent
Blum et al.

(10) Patent No.: US 8,913,804 B2
(45) Date of Patent: Dec. 16, 2014

(54) PROGRAMMING INTERFACE FOR SPINAL CORD NEUROMODULATION

(75) Inventors: David Arthur Blum, Boston, MA (US); Gregory T. Schulte, Minneapolis, MN (US); Scott Kokones, Boston, MA (US); Keith Carlton, Boston, MA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 571 days.

(21) Appl. No.: 13/160,104

(22) Filed: Jun. 14, 2011

(65) Prior Publication Data

US 2012/0014580 A1    Jan. 19, 2012

Related U.S. Application Data

(60) Provisional application No. 61/354,576, filed on Jun. 14, 2010, provisional application No. 61/376,439, filed on Aug. 24, 2010.

(51) Int. Cl.
*G06K 9/00* (2006.01)
*A61N 1/36* (2006.01)
*A61N 1/372* (2006.01)
*A61B 6/12* (2006.01)
*G06F 19/00* (2011.01)

(52) U.S. Cl.
CPC ........ *A61N 1/37235* (2013.01); *A61N 1/36182* (2013.01); *G06F 19/321* (2013.01); *G06F 19/3437* (2013.01); *A61N 1/37427* (2013.01); *A61N 1/36071* (2013.01); *G06F 19/324* (2013.01); *A61B 6/12* (2013.01)
USPC .............. 382/128; 382/132; 607/45; 607/116

(58) Field of Classification Search
USPC .............. 382/128, 132; 607/46, 117, 122, 45, 607/116
See application file for complete search history.

(56) References Cited

U.S. PATENT DOCUMENTS

| 7,346,382 | B2 | 3/2008 | McIntyre et al. |
| 7,734,340 | B2 | 6/2010 | De Ridder |
| 8,606,360 | B2 * | 12/2013 | Butson et al. ................... 607/45 |
| 8,620,452 | B2 * | 12/2013 | King et al. ................... 607/116 |
| 2005/0060009 | A1 | 3/2005 | Goetz |
| 2007/0162086 | A1 * | 7/2007 | DiLorenzo ...................... 607/45 |
| 2007/0288064 | A1 | 12/2007 | Butson et al. |

(Continued)

FOREIGN PATENT DOCUMENTS

WO    2011/159688 A2    12/2011

OTHER PUBLICATIONS

European Patent Office, International Search Report and the Written Opinion in International Application No. PCT/US2012/069667, dated Feb. 27, 2013 (15 pages).

(Continued)

*Primary Examiner* — Gregory M Desire
(74) *Attorney, Agent, or Firm* — Kenyon & Kenyon LLP

(57) ABSTRACT

A tool for assisting in the planning or performing of electrical neuromodulation of a patient's spinal cord. The tool may have various functions and capabilities, including calculating a volume of activation, registering an electrode(s) shown in a radiologic image, constructing functional images of the patient's spinal anatomy, targeting of neuromodulation, finding a functional midline between multiple electrodes, determining the three-dimensional position of multiple electrodes, and/or accommodating for electrode migration. In certain embodiments, the tool can be embodied as computer software or a computer system.

52 Claims, 12 Drawing Sheets

(56) References Cited

U.S. PATENT DOCUMENTS

| | | |
|---|---|---|
| 2009/0054950 A1* | 2/2009 | Stephens .................. 607/41 |
| 2009/0196472 A1 | 8/2009 | Goetz et al. |
| 2009/0287271 A1 | 11/2009 | Blum et al. |
| 2010/0023103 A1 | 1/2010 | Elborno |
| 2010/0030312 A1* | 2/2010 | Shen ........................ 607/122 |
| 2010/0135553 A1 | 6/2010 | Joglekar |
| 2010/0137944 A1 | 6/2010 | Zhu |
| 2010/0179562 A1* | 7/2010 | Linker et al. ............... 606/129 |
| 2012/0265268 A1* | 10/2012 | Blum et al. ................ 607/46 |

OTHER PUBLICATIONS

USPTO, International Search Report and the Written Opinion of the International Searching Authority, or the Declaration, mailed Dec. 29, 2011, from related International Application No. PCT/US2011/040329.

Wesselink, et al., "Analysis of Current Density and Related Parameters in Spinal Cord Stimulation," IEEE Transactions on Rehabilitation Engineering, vol. 6, No. 2, June 1998, pp. 200-207.

* cited by examiner

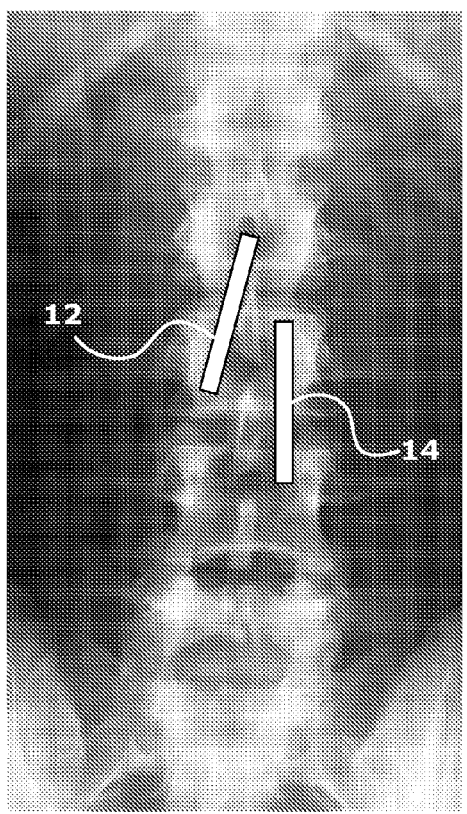 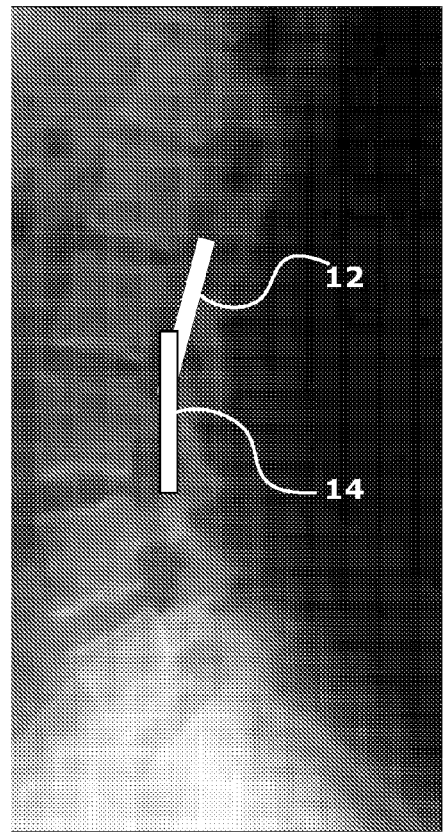
FIG. 1A                                FIG. 1B

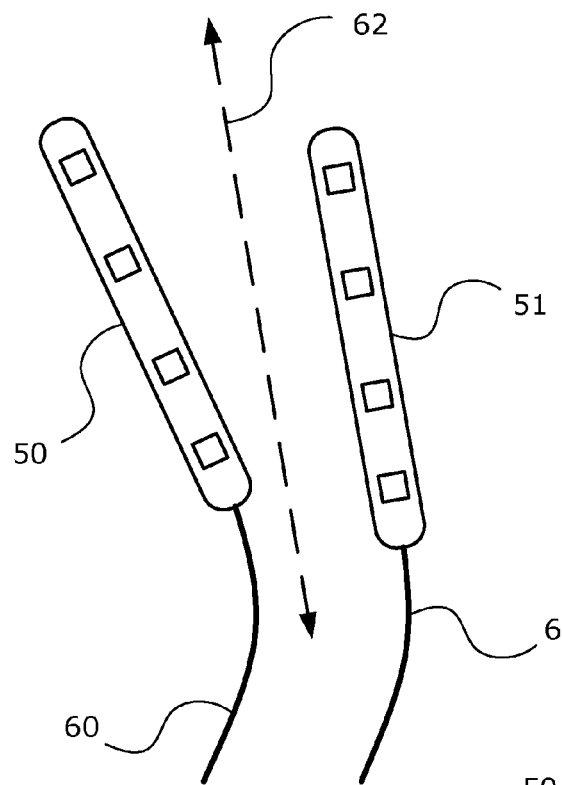
FIG. 8A
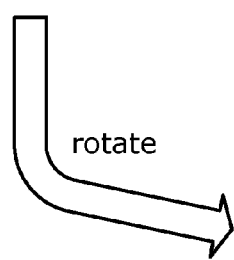
rotate
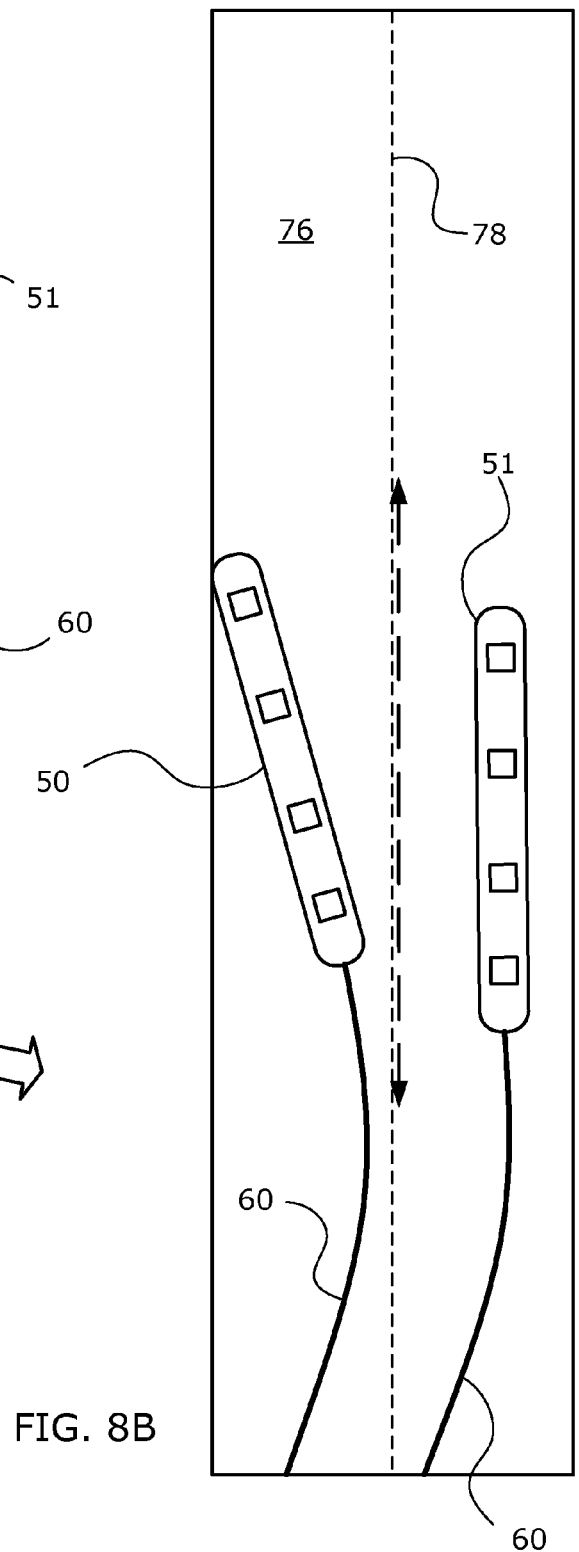
FIG. 8B

PROGRAMMING INTERFACE FOR SPINAL CORD NEUROMODULATION

CROSS-REFERENCE TO RELATED APPLICATIONS

The present application claims the benefit of priority to U.S. Provisional application Ser. Nos. 61/354,576, filed 14 Jun. 2010 and 61/376,439, filed Aug. 24, 2010, the entirety of each of which is hereby incorporated by reference herein.

TECHNICAL FIELD

The present invention relates generally to programming for electrical stimulation of the spinal cord.

BACKGROUND

Spinal cord stimulation can be used to treat chronic pain by providing electrical stimulation pulses from an electrode array implanted in close proximity to a patient's spinal cord. It is desirable to tailor the electrical stimulation parameters (such as electrode contact selection, polarity selection, pulse amplitude, pulse width, and pulse rate) for treatment of a particular patient. However, the process of selecting stimulation parameters can be time consuming and may require a great deal of trial-and-error before a suitable therapeutic program is found. Often, these parameters are selected based on intuition or some other idiosyncratic methodology. Because the programming of spinal cord stimulation can be such a cumbersome process, there is a need for assistance in the planning or performing of electrical stimulation of a patient's spinal cord.

SUMMARY

The present invention provides a tool for assisting in the planning or performing of electrical neuromodulation of a patient's spinal cord. The tool may be embodied as computer software or a computer system. In certain embodiments, the present invention provides a method for assisting the planning or performing of spinal cord neuromodulation in a patient, comprising: (a) having a functional image of the patient's spinal anatomy, wherein the functional image of the spinal anatomy includes an electrode and information defining functional regions of the spinal anatomy according to one or more neurologic functions; (b) determining the position of the electrode relative to the functional regions; (c) selecting a target functional region of the spinal anatomy; (d) having an electric field model of an electrode positioned adjacent the patient's spinal cord; and (e) determining one or more electrode neuromodulation settings that produces a volume of activation that at least partially encompasses the targeted functional region of the spinal anatomy.

In certain embodiments, the present invention provides a method for assisting the planning or performing of spinal cord neuromodulation in a patient, comprising: (a) receiving a first radiologic image of an electrode inside a patient, wherein the electrode is in a first position; (b) receiving a second radiologic image of the electrode after a change in the position of the electrode, wherein the electrode is in a second position; (c) determining the position of the electrode in the second position relative to the electrode in the first position; (d) calculating a first volume of activation generated by the electrode in the first position; and (e) determining an electrode neuromodulation setting for the electrode in the second position that produces a second volume of activation that at least partially encompasses the first volume of activation.

In certain embodiments, the present invention provides a method for assisting the planning or performing of spinal cord neuromodulation in a patient, comprising: (a) receiving a radiologic image of the patient showing one or more electrodes inside the patient; (b) locating the one or more electrodes in the radiologic image, wherein the one or more electrodes collectively have multiple electrode contacts; and (c) determining a functional midline for the one or more electrodes.

In certain embodiments, the present invention provides a method for assisting the planning or performing of spinal cord neuromodulation in a patient, comprising: (a) having an electric field model of an electrode positioned adjacent a spinal cord, wherein the model includes a representation of the depth of the cerebrospinal fluid between the electrode and the spinal cord; and (b) using the electric field model to calculate a volume of activation created by the electrode under a set of electrode neuromodulation conditions.

In certain embodiments, the present invention provides a method for assisting the planning or performing of spinal cord neuromodulation in a patient, comprising: (a) receiving a first radiologic image showing an electrode and a spinal anatomy of the patient; (b) receiving a second radiologic image showing the electrode and the spinal anatomy of the patient, wherein the second radiologic image provides a different view than the first radiologic image; and (c) using the first radiologic image and the second radiologic image to determine the three-dimensional position of the electrode in relation to the spinal anatomy.

BRIEF DESCRIPTION OF THE DRAWINGS

FIGS. 1A and 1B show x-ray images of a patient's spine with two electrodes that are implanted in the spine. FIG. 1A shows an anterior-posterior view and FIG. 1B shows a lateral view of the spine.

FIGS. 8A and 8B show an example of how the functional midline of the electrodes can be aligned with the physiologic midline of the spinal cord.

FIG. 12A shows the electrode prior to migration and FIG. 12B shows the electrode after migration.

DETAILED DESCRIPTION

Figure 2A:
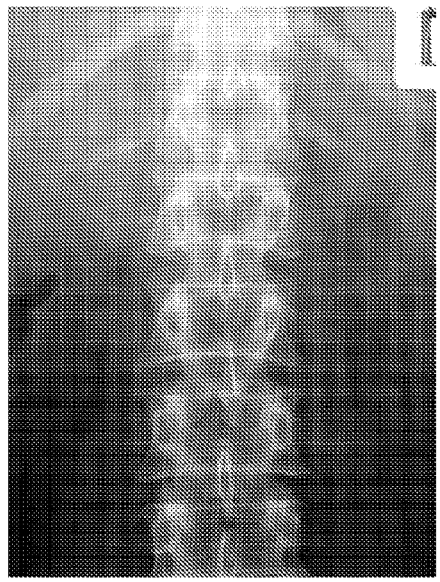
FIG. 2A shows an anterior-posterior view x-ray image of a patient's spine.

The present invention provides a tool for assisting in the planning or performing of electrical neuromodulation of a patient's spinal cord (sometimes referred to in the art as spinal cord stimulation). In certain embodiments, the tool provides a simulation of how much volume of neural tissue is affected by the electrical neuromodulation. As used herein, the term "volume of activation" means a volume of neural tissue in which the neurons are activated by the electric field being applied to the neural tissue during electrical neuromodulation. Neural activation may have a stimulatory effect or an inhibitory effect on the neural tissue, or a combination of both. Although the volume refers to a three-dimensional space, the calculation, analysis, and/or displaying of the volume as described herein does not necessarily have to be performed in three dimensions. Such actions may be performed in two dimensions instead. For example, the volume of activation may be calculated in a two-dimensional plane and shown as a two-dimensional image.

The present invention may use any suitable method for calculating a volume of activation for neural tissue. For example, methods for calculating a volume of activation suitable for use in the present invention include those described in U.S. Pat. No. 7,346,382 (McIntyre et al.), U.S. Patent Application Publication No. 2007/0288064 (Butson et al.), and U.S. Patent Application Publication No. 2009/0287271 (Blum et al.), which are incorporated in their entirety by reference herein. In certain embodiments, to calculate a volume of activation, the tool uses a mathematical model of the electric field generated by one or more electrodes positioned adjacent the spinal cord of a patient. The mathematical model may be any suitable type of model that can be used to model an electric field created by an electrode, such as finite element models of the electrode(s) and the tissue medium.

The electric field generated by an electrode is dependent upon various conditions of the electrode itself, including the electrode position, electrode orientation, electrode configuration, electrode contact polarity, electrode contact selection, electrode contact capacitance, electrode contact impedance, and waveform parameters (e.g., shape, pulse width, frequency, voltage, etc.). As used herein, "electrode neuromodulation conditions" refers to one or more of these factors. A set of electrode neuromodulation conditions may include one or more of these factors. For a given set of electrode neuromodulation conditions, the tool can calculate a volume of activation produced by the electrode. As used herein, the term "electrode neuromodulation settings" refers to a subset of electrode neuromodulation conditions that relate more specifically to the electrode contacts and can be adjusted during the operation of the electrode to vary the electric field. Examples of electrode neuromodulation settings include electrode contact selection and waveform parameters (e.g., shape, pulse width, frequency, voltage, etc.).

As used herein, the term "electrode" refers to the lead body along with the electrode contacts on the lead body. When referring to position, it is convenient to refer to the electrode as a whole, rather than referring to the position of the electrode contacts or lead body individually because the electrodes contacts are fixed on the lead body. Therefore, if the position of the electrode contacts relative to the lead body is known, then the position of the electrode contacts can be determined from the position of the lead body, and vice versa. Because of this fixed relationship, any reference to the position of the electrode is intended to include the position of the lead body and the electrode contacts as well. Also, when referring to the "position" of the electrode, this is intended to include the orientation of the electrode as well.

The electric field model can be solved for the spatial and temporal voltage distribution that represents the electric field that is created in the tissue medium by the electrode according to a particular set of electrode neuromodulation conditions. In certain embodiments, the electric field model is coupled to a neuron model to determine whether the electric potential at a given point in space is sufficient to activate neurons in the tissue medium. The boundaries of neuronal activation predicted by the neuron model determines the volume of activation. Examples of such methods that can be used in the present invention include those described in U.S. Pat. No. 7,346,382 (McIntyre et al.), U.S. Patent Application Publication No. 2007/0288064 (Butson et al.), and U.S. Patent Application Publication No. 2009/0287271 (Blum et al.), which are incorporated by reference herein. Where radiologic imaging of the spinal anatomy is available, the model axons of the neuron model can be aligned to the orientation of the spinal cord or spinal column.

Another way in which the volume of activation can be determined is by calculating the second order spatial derivative of the electric potential that is distributed around the electrode. The second spatial derivative is then compared against an activation threshold. The activation threshold is the threshold value at which a neuron is activated at that particular point in space for the tissue medium. If the second spatial derivative of the electric potential exceeds the activation threshold, then the neuron at that point in space is considered to be activated. The second order spatial derivative can be calculated by numerical or approximation techniques. For example, the second difference of the electrical potential can be used to approximate the second order derivative, as described in U.S. Pat. No. 7,346,382 (McIntyre et al.), U.S. Patent Application Publication No. 2007/0288064 (Butson et al.), and U.S. Patent Application Publication No. 2009/0287271 (Blum et al.), which are incorporated by reference herein.

These activation thresholds are determined from the application of the calculated electric field to the neuron model, as described above. However, the manner in which the activation thresholds are provided can vary according to different embodiments of the present invention. In some embodiments, these activation thresholds can be calculated during the operation of the tool. However, it is also possible to have these activation thresholds calculated prior to the operation of the tool. In this case, the activation thresholds are predefined for use during the operation of the tool. For example, based on the pre-calculations, equations may be formulated that give the activation thresholds as a function of distance from the electrode and one or more electrode neuromodulation conditions (such as pulse width and voltage). Thus, during operation of the tool, the tool may use one or more of these equations to calculate the activation thresholds by inputting the relevant values into the equation and solving the equations to obtain a spatial map of the activation thresholds. Thus, based on a given set of neuromodulation conditions, the spatial contour of the activation thresholds can be established and used to determine the volume of activation as the isosurface where the second spatial derivative is suprathreshold. In addition to these methods, other methods for determining a volume of activation by an electrode can be used in the present invention, such as those methods described in U.S. Patent Application Publication No. 2007/0288064 (Butson et al.) and U.S. Patent Application Publication No. 2009/0287271 (Blum et al.), which are incorporated by reference herein.

Electrode Registration

In certain embodiments, the tool may use a radiologic image in performing the functions that are described herein. The radiologic image may show the electrodes and/or various portions of the patient's spinal anatomy. As used herein, "spinal anatomy" means the anatomy relating to the spinal column, which includes the spinal cord, the vertebral bodies, nerves, and/or other soft or bony tissue of the spinal column. The radiologic image may be any type of body imaging used in medicine, such as x-rays (including conventional film and fluoroscopic x-rays), magnetic resonance imaging (MRI), computed tomography (CT), positron emission tomography (PET), etc. For example, the radiologic image may be an anterior-posterior view or a lateral view x-ray of the patient's spine. The radiologic image may not necessarily show all portions of the spinal anatomy. The portion of the patient's spinal anatomy that is visible on the radiologic image will depend upon the type of imaging modality used. For example, in x-ray images, only the bony structures may be visible in the image (but not the spinal cord itself). In MR images, the spinal cord itself may be visible, in addition to the bony and other soft tissue elements.

In the tool, the radiologic images are embodied as data structures (e.g., digital images). In some cases, the radiologic image may be used to register the location of the electrode. For example, the tool may register the electrode relative to a landmark of the spinal anatomy that is visible on the radiologic image. For example, in the case of x-ray images, the location of the electrode can be registered relative to the vertebral bodies that are visible on the image. As will be explained below, the location of the electrode relative to the spinal cord itself can be estimated based on the association between the vertebral level and the spinal cord level.

As explained above, when referring to position, it is convenient to refer to the electrode as a whole, rather than referring to the position of the electrode contacts or lead body individually because the electrode contacts are fixed on the lead body. As a result, if the position of the lead body is registered by the tool, then the electrode contacts on the lead body can also be considered to be registered as well, and vice versa. Whether the tool will locate the lead body or the electrode contacts directly will depend on a variety of factors, such as its visibility in the radiologic image. Since the lead body is larger, in some cases, it may be more practical to locate the lead body and then locate the position of the electrode contacts based on the lead body position. In other cases, since the electrode contacts may be more radiopaque and more readily identifiable on CT or x-ray, it may be more practical to locate the electrode contacts in the image.

The electrode can be located automatically or manually in the radiologic image. Example methods of locating and registering an electrode that can be used in the present invention are described in U.S. Patent Application Publication No. 2009/0287271 (Blum et al.), which is incorporated by reference herein.

Where there are multiple electrodes (two or more) present in the radiologic image, the tool may determine the position of the electrodes in relation to each other and/or the spinal anatomy. In some cases, three-dimensional positional information can be reconstructed from multiple (two or more) different two-dimensional views of the electrode and the angle between the different views. This three-dimensional reconstruction can be performed using any suitable technique known in the art.

For example, FIGS. 1A and 1B show x-ray images that can be used to locate and reconstruct the three-dimensional position of two electrodes 12 and 14 that have been implanted in a patient's spine. FIG. 1A shows an anterior-posterior view of the spine with electrodes 12 and 14 visible in the x-ray image. The tool registers the position of electrodes 12 and 14 relative to each other and/or the spinal anatomy.

FIG. 1B shows a lateral view of the spine with electrodes 12 and 14 visible in the x-ray image. The tool registers the position of electrodes 12 and 14 relative to each other, and optionally, with the spinal anatomy. Having these two different perspective views (at a 90° angle) of electrodes 12 and 14, the tool can now reconstruct the three-dimensional position of electrodes 12 and 14 relative to each other, and optionally, the spinal anatomy. Thus, the tool can display a reconstructed three-dimensional view of electrodes 12 and 14 with respect to each other and/or the spinal anatomy.

Thus, in certain embodiments, the tool may receive a first radiologic image (e.g., an anterior-posterior view x-ray) showing an electrode and the spinal anatomy of the patient, and receive a second radiologic image (e.g., a lateral view x-ray) showing the electrode and the spinal anatomy of the patient. The second radiologic image provides a different view than the first radiologic image so that they can be used to determine the three-dimensional position of the electrode in relation to the spinal anatomy. In some cases, the first and second radiologic images are used to determine the three-dimensional position of the multiple electrodes in relation to each other. Once the position of the electrodes is determined, a three-dimensional image of the electrodes and the spinal anatomy may be displayed to the user. The three-dimensional image may be rotated, panned, and zoomed to allow the user to precisely explore the actual device positioning in space.

Functional Images

In certain embodiments, in addition to anatomical structures, the radiologic image of the spinal anatomy may include information associating parts of the image to one or more neurologic functions (i.e., a functional image). The functional image may also include other symbolic information, such as structure names, object features, target volumes generated from previous patient data, anatomic landmarks, or boundaries. The neurologic functions in the functional image may be either motor or sensory functions. In some cases, the functional image may define different levels of the spinal cord in the image. For example, the functional image may include information that associates different parts of the image with the dermatomes that are innervated by the different spinal cord levels, as will be further explained below.

Functional information can be incorporated into the image data using any suitable technique known in the art. In some cases, the functional information is incorporated by registering a patient-specific radiologic image to a standard atlas of the same anatomy. A standard atlas is an atlas of the spinal anatomy that is intended to represent the typical or normal anatomy that is present in human beings. As such, the standard atlas can be derived from a composite of the anatomy of multiple individuals to be representative of "normal" or "typical" human anatomy. The tool may have multiple standard atlases (e.g., variants of normal anatomy) and allow the user to select one that is a closest match to the patient being treated.

Registration of the patient-specific image to the standard atlas may be performed using any suitable technique known in the art, including the methods described in U.S. Patent Application Publication No. 2009/0287271 (Blum et al.). For example, the image registration process may involve a transformation of the patient-specific image to match or fit the standard atlas, a transformation of the standard atlas to match or fit the patient-specific image, or some combination of both. In some cases, the image registration process may use anatomic landmarks that have been established in the image. These anatomic landmarks can be identified manually by a user or automatically by the tool. For example, in an x-ray of the spine, the vertebral bodies may be identified and registered into the image. Once the anatomic landmarks are identified, the patient-specific radiologic image can be scaled or morphed to fit the standard atlas using the transformation process described above.

Figure 2B:
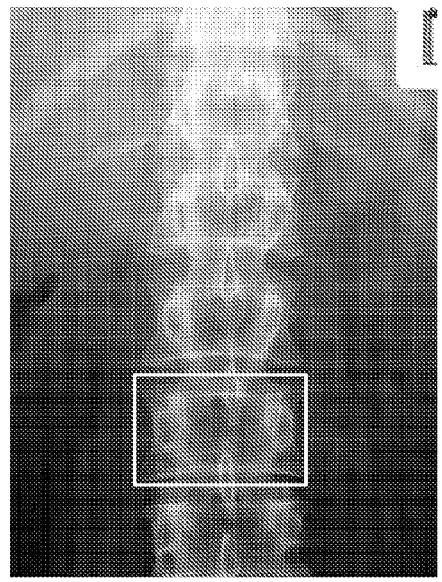
FIG. 2B shows the user identifying a vertebrae.

For example, FIG. 2A shows an x-ray image of a patient's spine, which is imported into the tool. The spinal cord is not visible on the x-ray, but is located within the vertebral spine (i.e., spinal column), which is made up of a column of vertebral bodies (vertebrae). As seen in FIG. 2B, the user identifies the different vertebrae that are visible on the x-ray image by drawing a box around each of the vertebrae. The spinal cord itself is functionally divided into segmental levels defined by the spinal roots that enter and exit the spinal column between each of the vertebral body levels.

Figure 3:
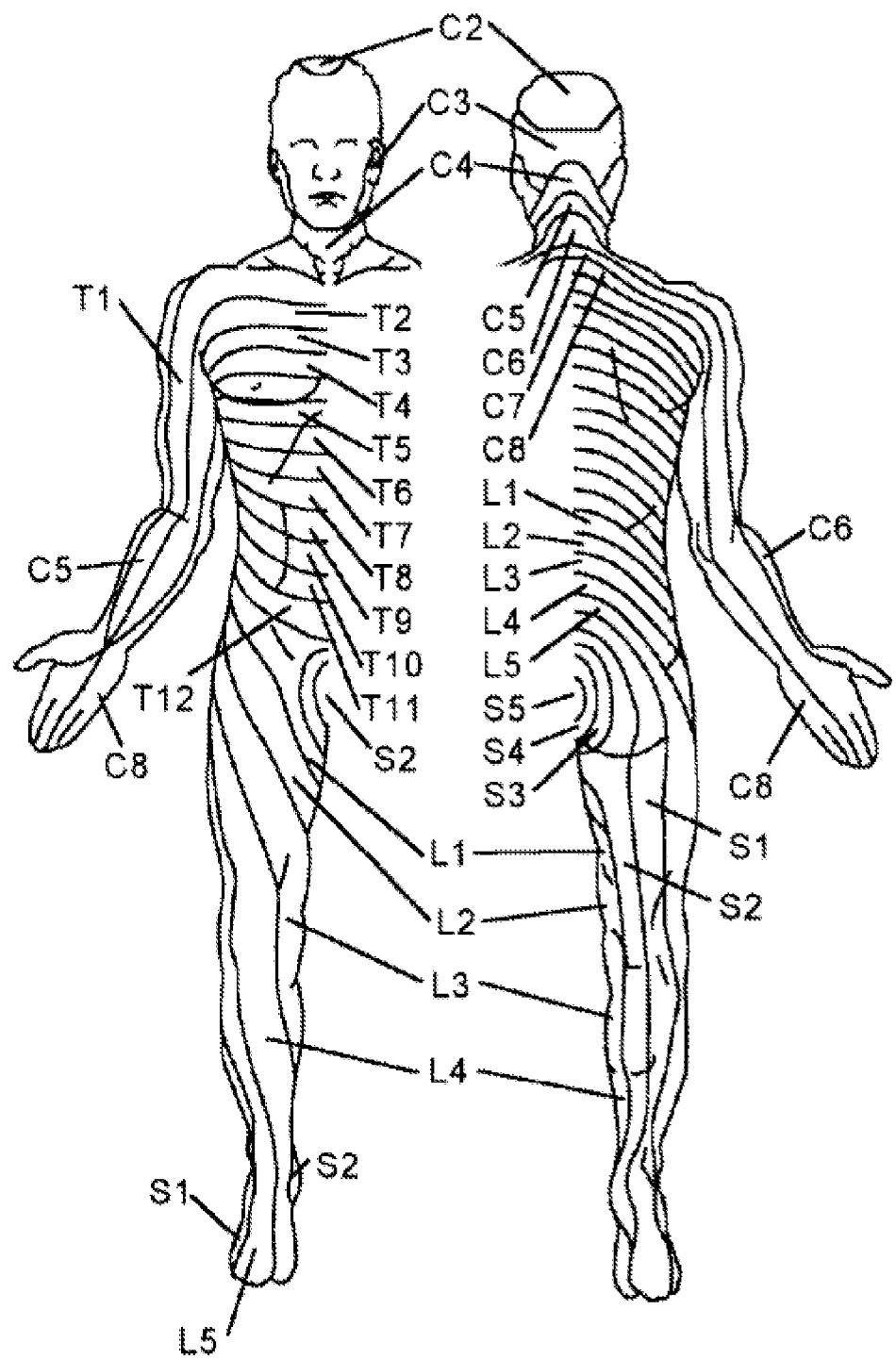
FIG. 3 shows a dermatome map of the human body.

A dermatome is an area of the skin that is predominantly innervated by nerves originating from a single spinal level. FIG. 3 shows a dermatome map of the human body. Thus, the spinal cord can be divided functionally into segments that correspond to different dermatomes. The spinal cord segmental levels do not necessarily correspond to the same level of the vertebral body. Accordingly, the dermatomes innervated by the different spinal cord levels do not necessarily correspond to the vertebral levels. For example, the L5 dermatome level for low back pain may correspond to the T10 vertebral level. However, based on known anatomic and physiologic relationships, the tool of the present invention can make the appropriate correlation between the dermatome levels, the spinal cord levels, and/or the vertebral levels. This association may be useful where the vertebral bodies are being used as a reference for the position of the electrode.

Figure 2C:
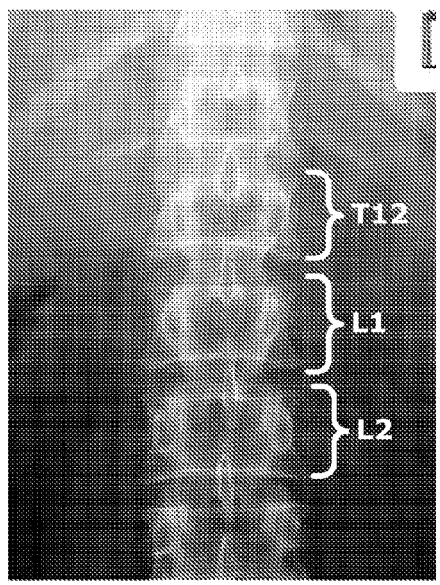
FIG. 2C shows the registration of spinal cord levels into the x-ray image.

As seen in FIG. 2C, the association of these different vertebral levels with their spinal cord levels are registered into the image to create a functional image in which spinal cord levels T12, L1, and L2 are registered as functional regions in the image in association with the vertebral levels that are visible in the image. If electrodes are also present in the image, the electrodes can also be identified (either manually or automatically) and their position registered in relation to the functional regions.

As an alternative to having the user identify each vertebra, the positions of the vertebrae may be identified based on a user identification of a single vertebra in an image. For example, the user may input a vertebral outline, or part of a vertebral outline, along with an identification of the vertebra to which the outline corresponds (e.g., T1). The image is then analyzed to extrapolate the positions of the remaining vertebrae based on their relative positions to the outlined vertebra.

Targeting of Neuromodulation

In certain embodiments, the tool can be used to select a region of the spinal cord as a target for electrical neuromodulation. The selection of the target region can be provided in any suitable manner. For example, the targeted region can be input by the user as a specific anatomic structure (such as a vertebral level), a segment of the spinal cord, a dermatome level, or an area of the body where the patient is experiencing pain or discomfort. In the example where the user indicates one or more dermatome levels as a targeted region, the tool may determine the spinal cord level(s) and/or vertebral level(s) that correspond to those dermatomes. In the example where the user indicates where the patient is experiencing pain or discomfort, the tool may determine the one or more dermatomes associated with that part of the body, and then select one or more spinal cord levels and/or vertebral levels that correspond to that dermatome.

Having selected the targeted region, the tool can then find a set of electrode neuromodulation conditions that would direct the electrical neuromodulation to that targeted region by comparing the predicted volumes of activation against the targeted region. For example, the tool may use a scoring technique that measures the effectiveness of the neuromodulation based on how much of the predicted volume of activation encompasses the targeted region, how much of the targeted region is within the predicted volume of activation, how much of the predicted volume of activation is outside the targeted region, how much of the targeted region is outside the predicted volume of activation, how much of the predicted volume of activation encompasses neural tissue that would cause side effects, or a combination thereof. The tool may calculate multiple predicted volumes of activation under different neuromodulation conditions in order to find a suitable set of electrode neuromodulation conditions. When a combination of scoring factors is used, the different factors may be weighted differently according to their relative importance in determining the therapeutic effectiveness of the neuromodulation. In some cases, an improved or optimal set of neuromodulation conditions can be determined by using an optimization algorithm to find a set of electrode neuromodulation conditions that produces a volume of activation having the best score (e.g., highest or lowest score).

Figure 4:
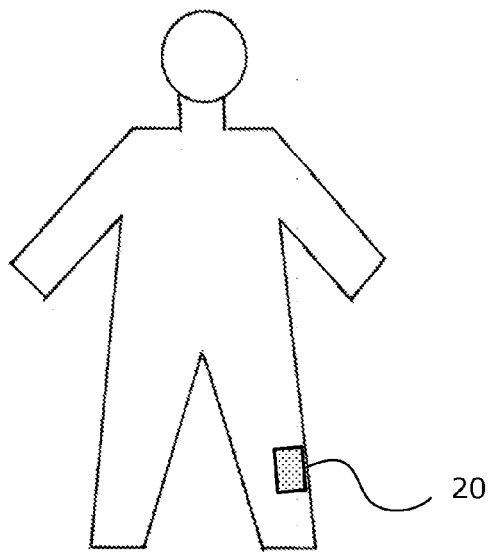
FIG. 4 shows a human figure that may be displayed by the tool with the area of pain indicated in the human figure.
Figure 5:
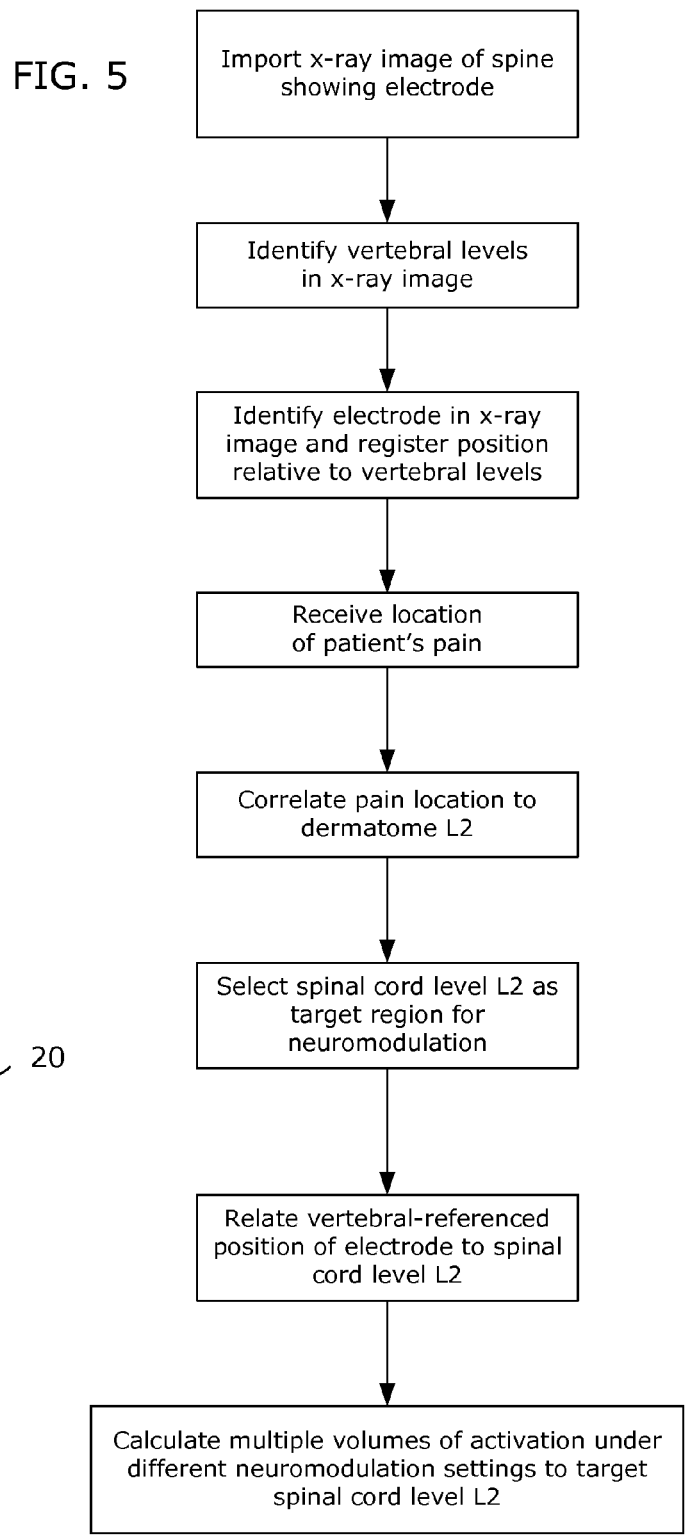
FIG. 5 shows a flowchart illustrating an example of how spinal cord neuromodulation can be targeted based on the location of the pain on a patient's body.
Figure 6:
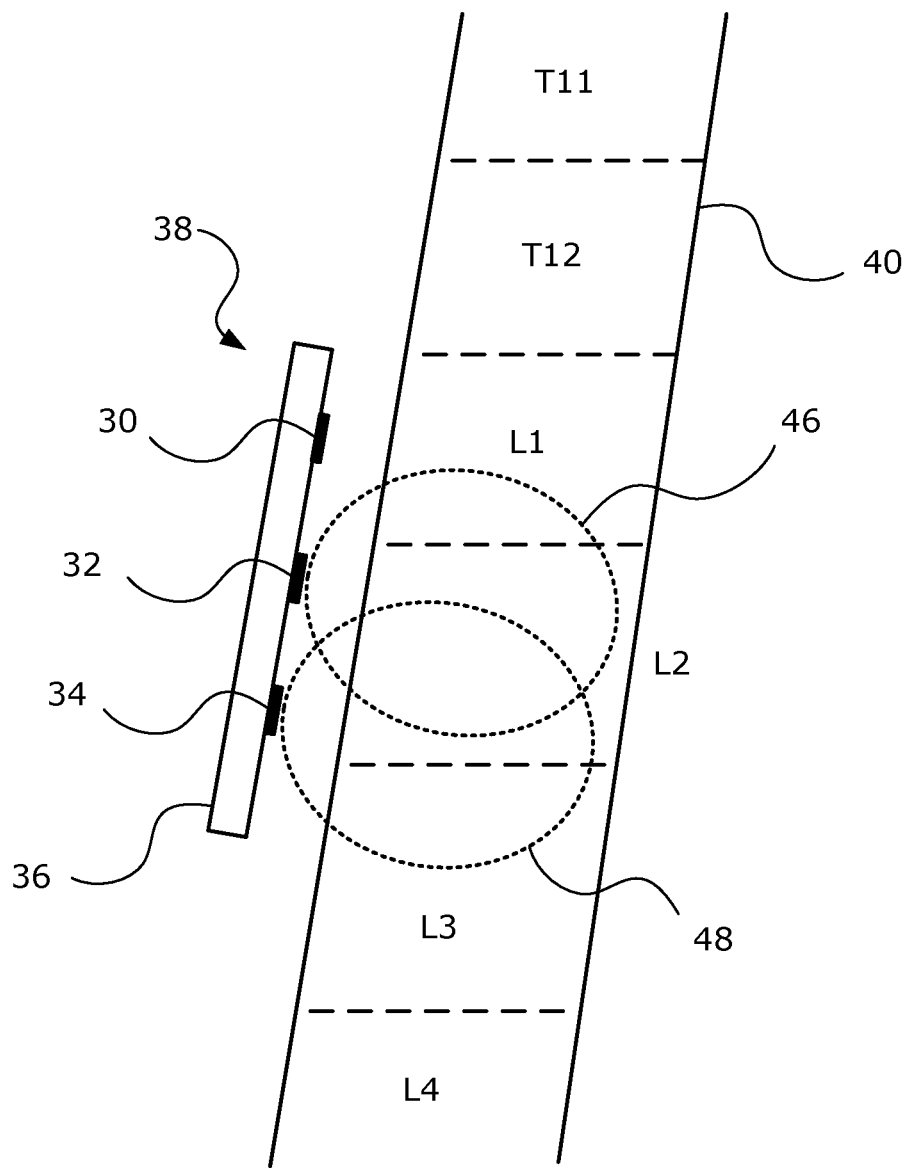
FIG. 6 shows an example of spinal cord neuromodulation being targeted to a specific spinal cord level.

For example, FIG. 4 shows a patient that is experiencing pain in area 20 of their body. The user (e.g., the patient or a caretaker) enters the location of area 20 into the tool and the tool correlates this area 20 with the L2 dermatome level on the left side, and then correlates the left-side L2 dermatome level with the corresponding region the spinal cord or the vertebral level that corresponds to the L2 level of the spinal cord. FIG. 6 shows an image of the spinal cord 40 with the spinal cord levels being represented as different functional regions in the spinal cord (levels T11-L4 being shown here). Adjacent the spinal cord 40 is an electrode 38 having three electrode contacts 30, 32, and 34 fixed on a lead body 36. Based on the user's input, the functional region L2 of spinal cord 40 is selected as the target region for electrical neuromodulation. Accordingly, the tool determines a set of electrode neuromodulation settings that would create a volume of activation that is directed to functional region L2. In this instance, the set of electrode neuromodulation settings includes the selection of electrode contacts 32 and 34 for activation, and electrode contact 30 for non-activation. Additionally, with this selected set of electrode neuromodulation settings, electrode 32 is predicted to create a volume of activation 46 and electrode 34 is predicted to create a volume of activation 48. Thus, with the combination of volume of activations 46 and 48, the selected set of electrode neuromodulation settings create a volume of activation that is directed to dermatome level L2 of the spinal cord. FIG. 5 shows a flowchart illustration of the above process.

Dermatome targeting using patient feedback about where the electrically-induced parasthesia is located in their body may not always be reliable because the patient's sensory perception may not be accurate or the patient may not sense sufficient parasthesia from the electrical neuromodulation. In certain embodiments, the dermatome location of the electrical neuromodulation can be localized more precisely using electromyography (EMG). For EMG localization of electrical neuromodulation, a number of EMG electrodes are placed on the patient's body. Electrical neuromodulation of the sensory fibers in the spinal cord can elicit a reflexive motor response and these motor responses can be detected as EMG signals in the specific dermatomes. Thus, by analyzing the EMG signals during electrical neuromodulation, the dermatome location of the electrical neuromodulation can be identified more precisely, thus allowing more accurate targeting of electrical neuromodulation.

In certain embodiments, the electrode used in the neuromodulation may also have recording electrodes which can sense neural signals passing through sensory nerve fibers. This can be useful for improved accuracy in identifying where the patient is experiencing pain or discomfort. The sensory signals passing through these sensory fibers may be produced by applying a sensory stimulation to the area where the patient is feeling the pain or discomfort. A variety of different kinds of sensory stimulations can be used, such as applying a dull touch, a sharp prick, or a slight electrical pulse to the skin. The recording electrode could sense this signal being transmitted along nearby sensory fibers as an increase in local field potential. Based on which recording contact records the strongest signal, or based on the distribution of the signal across multiple contacts, the fiber(s) carrying the sensory stimulation signal from the afflicted dermatome is identified. Moreover, the strength of the signal can be used to determine the magnitude of the patient's pain or discomfort in that area.

Cerebrospinal Fluid

One of the factors influencing the electric field generated by an electrode is the electrical conductivity of the surrounding tissue medium (e.g., the electrical conductivity of the spinal cord neural tissue or other body tissue in the vicinity of the electrode, such as cerebrospinal fluid, tissue membranes, encapsulation tissue around the electrode, etc.). Thus, the electric field model used by the tool may include a characterization of the tissue electrical conductivity. In some cases, different anatomical structures may be represented as having different electrical conductivities in the electric field model. One of the tissue mediums that may be relevant in spinal cord neuromodulation is the cerebrospinal fluid (CSF) that surrounds the spinal cord. The CSF is considered to be relatively more electrically conductive compared to the other surrounding tissue.

In certain embodiments, the electric field model may account for the amount of CSF that is present between the electrode and the spinal cord. For example, the electric field model may account for the thickness (in dimensional terms, not viscosity) of the CSF between the electrode and the spinal cord. The dimensional thickness of the CSF can be determined using various approaches. In some cases, the thickness of the CSF can be determined by using a radiologic image, such as an axial view MR image. In some cases, the thickness of the CSF can be approximated based on the electrode position relative to the spinal anatomy. For example, the thickness of the CSF can be approximated based on the vertebral level where the electrode is positioned or the size of the vertebrae where the electrode is positioned (in general, the size of the vertebral bodies progressively increase moving from the cervical to the lumbar spine). Accounting for the electrical conductivity of CSF may allow the tool to calculate a more accurate the volume of activation.

Total Potential Volume of Activation

In certain embodiments, the tool can show the total potential volume of activation capable of being produced by an electrode at a given position. The total potential volume of activation can be displayed as the overlap of the volume of activations produced by the highest tolerable amplitude anode/cathode pulse for each electrode. Knowing the total potential volume of activation may be useful during initial surgical implantation of the electrode to help position the electrode at a location that will meet both current and possible future coverage needs (e.g., accounting for the possibility of electrode migration, worsening pain, or wider extent of pain). The feature can also be useful for quickly seeing how much area has been tested by overlaying a history of stimulated regions and the total potential volume of activation. This feature can also allow the user to view spaces that are outside the potential volume of activation for a given electrode placement. For example, if two electrodes are staggered or canted, they may leave regions of the spinal cord unable to be reached by electrical neuromodulation. Displaying the total potential volume of activation would allow this to be realized during intraoperative or postoperative programming.

This display of the total potential volume of activation can be turned on and off, and may appear in a variety of colors, gradients, and patterns to best suit visualization. In addition, it may be layered with current neuromodulation settings or previously trialed settings to compare the total potential volume of activation with volumes already tested. As with other display features, the total potential volume of activation can be displayed as a two-dimensional area on a spinal cord or as a three-dimensional volume. The total potential volume of activation may also be used to predict dermatome regions capable of neuromodulation, which would then be displayed on a two-dimensional or three-dimensional representation of the spinal cord. The total potential volume of activation could also be shown as all the dermatome regions capable of being affected by the neuromodulation, which could be displayed on an image of a human figure.

Functional Midline

When multiple electrodes (two or more) are implanted into a patient, the electrodes are often not parallel to each other or not in level alignment with each other (e.g., one is higher than the other), and moreover, the position of the electrodes relative to the spinal cord is often not known since the spinal cord may not be visible on x-ray images. Where multiple electrodes are being modeled by the tool, the tool may determine a functional midline in the neuromodulation space around the electrodes. The functional midline is an imaginary line running in the neuromodulation space of the electrodes, which corresponds to the sensory midline of the patient's body, and which could be aligned to the physiologic midline of the patient's spinal cord. The functional midline is established by finding a set of neuromodulation settings that induces parasthesia in the center of the patient's body. The functional midline can then be derived from the relative pulse intensities between the multiple electrodes. The tool may also determine the functional midline for a paddle-type electrode having an array of electrode contacts on a single electrode lead or a single electrode that is implanted in a lateral orientation.

Figure 7A:
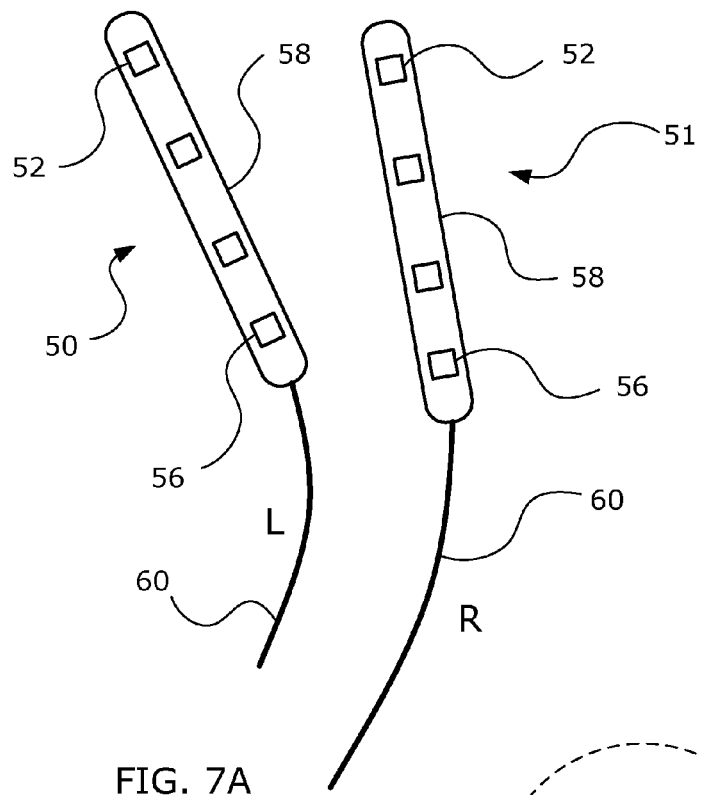
FIGS. 7A and 7B demonstrate an example of how the functional midline of two electrodes can be determined.
Figure 7B:
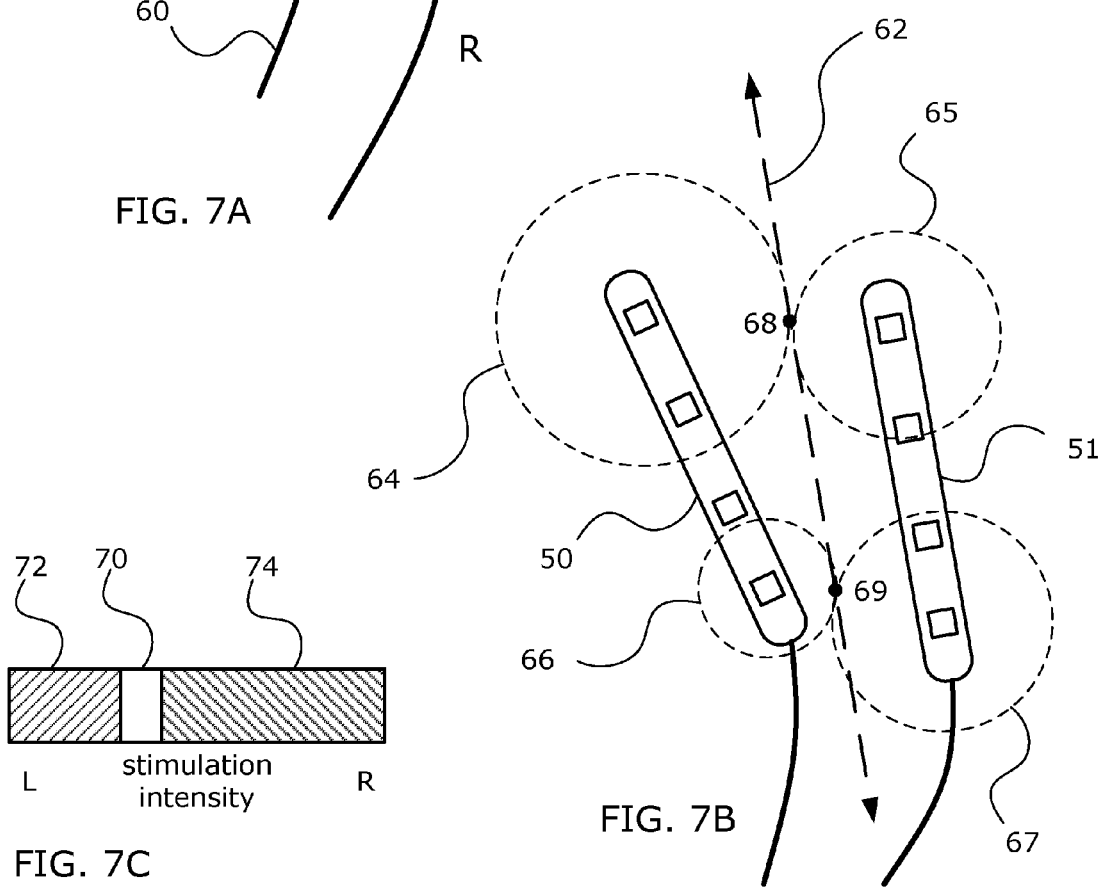

An example of how this may be performed is illustrated in FIGS. 7A and 7B. FIG. 7A shows two electrodes, 50 on the left side and 51 on the right side, each comprising a lead body 58 connected to lead wires 60 and having three electrode contacts, including top-most contacts 52 and bottom-most contacts 56. The functional midline is determined by finding the functional midpoint between the left and right top-most electrode contacts 52, and the left and right bottom-most electrode contacts 56. The functional midpoint between the left and right top-most electrode contacts 52 is determined by varying the relative pulse intensities (monopolar) between the left and right top-most electrode contacts 52, and receiving patient feedback of where the parasthesia is being sensed.

Figure 7C:
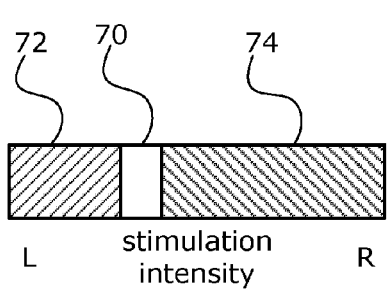
FIG. 7C shows a slider bar that may be used by the tool for adjusting spinal cord neuromodulation.

FIG. 7C shows how the stimulation field can be shifted to the left or right using a slider 70 displayed by the tool. Slider 70 is inside a bar that represents the left versus right relative pulse intensity. Area 72 in the bar corresponds to the relative pulse intensity for the electrode contact on the left electrode and area 74 in the bar corresponds to relative pulse intensity for the counterpart electrode contact on the right electrode. Slider 70 can be moved left or right to adjust the pulse intensity that is apportioned between the left and right electrode contacts. As an initial setting, the slider may be positioned in the middle such that half of a tolerable pulse intensity is sent to each of the counterpart electrode contacts on the left and right electrodes.

Figure 10:
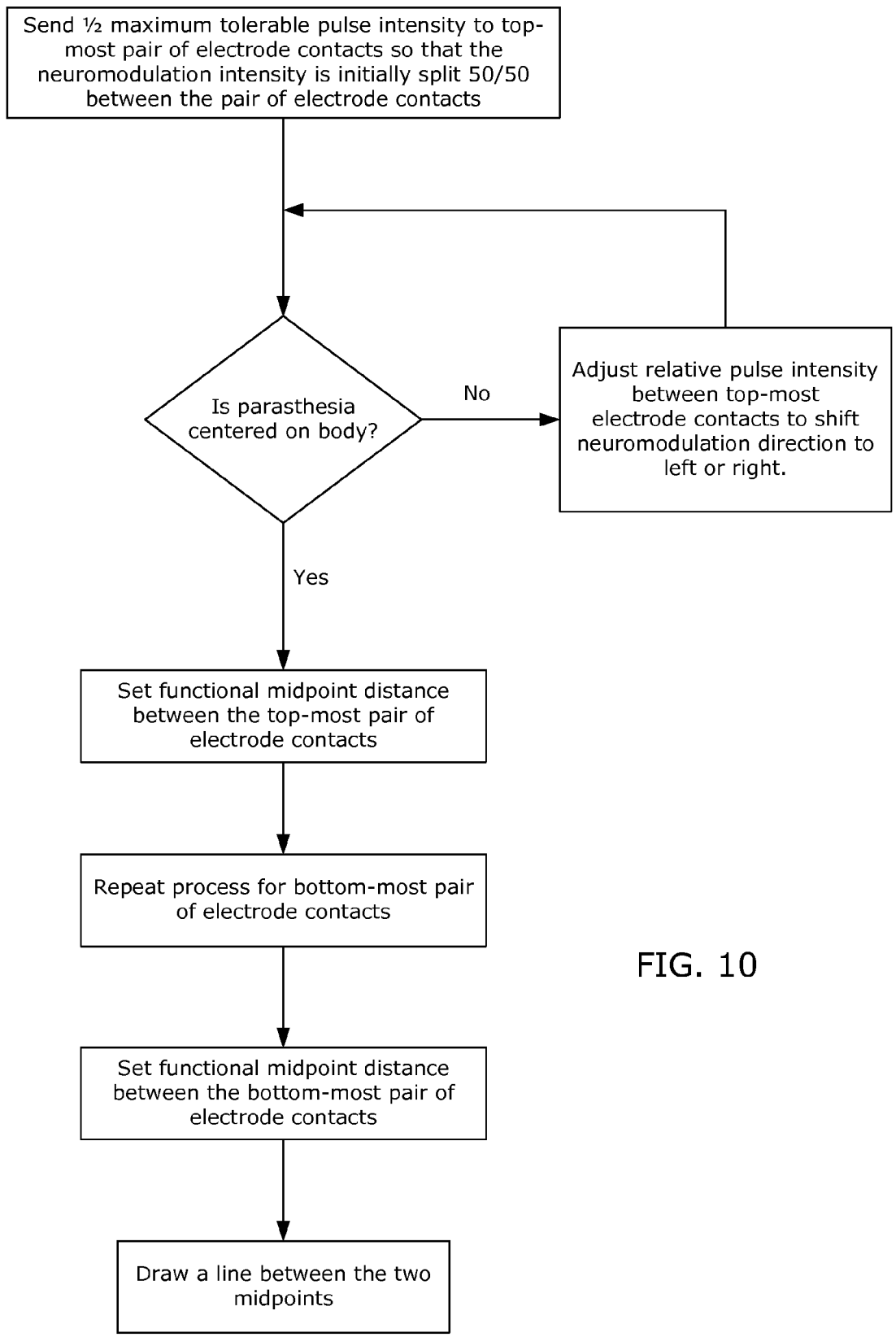
FIG. 10 shows a flowchart illustrating an example of how the functional midline of two electrodes can be determined.

When the patient indicates that the parasthesia is being sensed in the center of their body, the relative pulse intensities of the left and right top-most electrode contacts 52 gives the proportionate distance of the functional midpoint from the respective left and right electrode contacts 52. As shown in FIG. 7B, the patient's parasthesia has been centered for the top-most electrodes 52 when the left top-most electrode contact has a pulse intensity 64 and the right top-most electrode has a pulse intensity 65, with the functional midpoint being at point 68. Pulse intensities 64 and 65 do not represent actual activation fields, but is being used only to help illustrate how the left versus right relative pulse intensities can differ and be used to find the midpoint. The same process of varying the left/right relative pulse intensities and receiving patient feedback about the location of the parasthesia is repeated to find the functional midpoint for the bottom-most electrode contacts 56. In this instance, the patient's parasthesia has been centered for the bottom-most electrodes 56 when the left bottom-most electrode contact has a relative pulse intensity 66 and the right bottom-most electrode contact has a relative pulse intensity 67, with the functional midpoint being at point 69. An imaginary line is drawn between functional midpoints 68 and 69, and this imaginary line is the functional midline 62 between electrodes 50 and 51. FIG. 10 shows a flowchart illustration of the above process.

Figure 9:
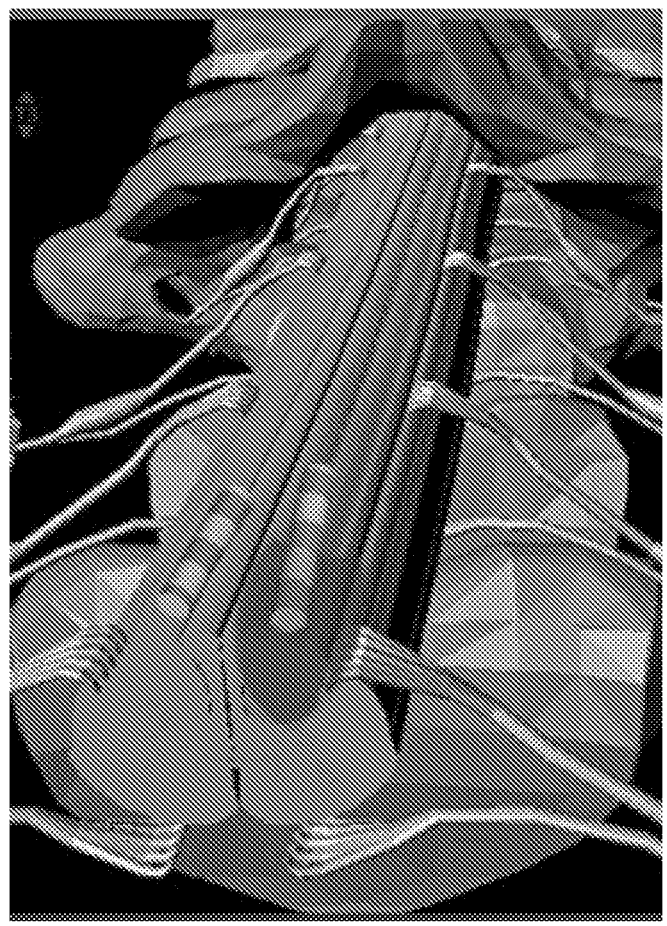
FIG. 9 shows an example of how electrodes can be displayed with an image of the spinal cord.

Once the functional midline is determined, this information can be used in various ways to assist in electrical neuromodulation of a patient's spinal cord. One use for the functional midline is for aligning the electrodes with respect to the physiologic midline of the spinal cord. For example, FIG. 8A shows the two electrodes 50 and 51 again with their functional midline 62. Based on this functional midline 62, the position (including orientation) of electrodes 50 and 51 can be aligned with a spinal cord. FIG. 8B shows a graphically rendered, generic image of a spinal cord 76 (not specific to any particular patient), with its physiologic midline represented by dotted line 78. By rotating the pair of electrodes 50 and 51, their functional midline 62 is made to be oriented parallel to physiologic midline 78 of spinal cord 76. The two electrodes 50 and 51 are displayed over spinal cord 76 to give a more accurate representation of how the electrodes 50 and 51 are oriented relative to the actual patient's spinal cord. FIG. 9 shows another example of how electrodes and a graphically rendered, generic image of a spinal cord could be displayed by the tool.

Thus, in certain embodiments, the tool receives a radiologic image of the patient showing one or more electrodes inside the patient and locates the one or more electrodes in the radiologic image. The one or more electrodes collectively have multiple electrode contacts. The tool determines the functional midline for the one or more electrodes and may display on a display screen, an image of a spinal cord and the one or more electrodes such that the functional midline of the one or more electrodes is aligned to the physiologic midline of the spinal cord.

In some cases, the tool may receive information about the relative electrical neuromodulation intensity between a first electrode contact among the multiple electrode contacts and a first counterpart electrode contact among the multiple electrode contacts. Based on the relative electrical neuromodulation intensities, the tool can determine a first midpoint between the first electrode contact and the first counterpart electrode contact. The tool may further receive information about the relative electrical neuromodulation intensity between a second electrode contact among the multiple electrode contacts and a second counterpart electrode contact among the multiple electrode contacts. Based on the relative electrical neuromodulation intensities, the tool can determine a second midpoint between the second electrode contact and the second counterpart electrode contact. The functional midline can be established as the line between the first midpoint and the second midpoint. This method may be applied to a single electrode (e.g., a paddle-type electrode having multiple electrode contacts arranged in an array) or multiple separate electrodes.

In cases where there are multiple separate electrodes (which collectively have multiple electrode contacts), a functional midline may be found using a first electrode contact which is on a first one of the multiple electrodes and a first counterpart electrode contact on a second one of the multiple electrodes. Based on the relative electrical neuromodulation intensities, the tool can determine a first midpoint between the first electrode contact and the first counterpart electrode contact. Furthermore, the tool may receive information about the relative electrical neuromodulation intensity between a second electrode contact on the first one of the multiple electrodes and a second counterpart electrode contact on the second one of the multiple electrodes. Based on the relative electrical neuromodulation intensities, the tool can determine a second midpoint between the second electrode contact and the second counterpart electrode contact; and establish the functional midline as a line between the first midpoint and the second midpoint.

Adaptive Searching

The functional midline can also be used to assist in targeting of the spinal cord neuromodulation to the appropriate side of the body (right vs. left side). Based on whether the patient's symptoms are on the left or right side of their body, the electrical neuromodulation to the spinal cord can be directed to the same side (left or right) of the functional midline. This targeting may be implemented through a binary searching algorithm.

Figure 11A:
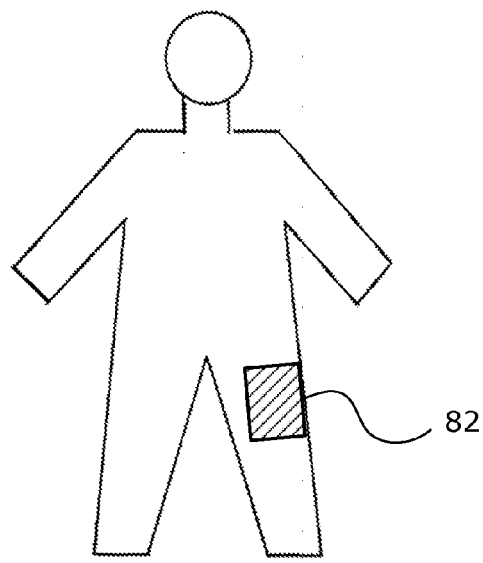
FIGS. 11A-11D show an example of how the tool can use the functional midline for targeting of spinal cord neuromodulation.
Figure 11B:
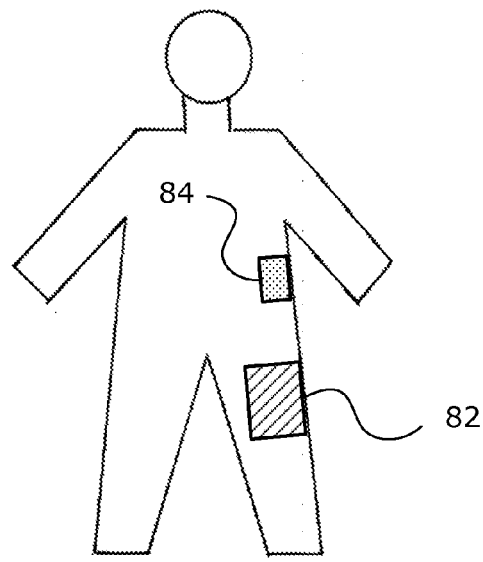
Figure 11C:
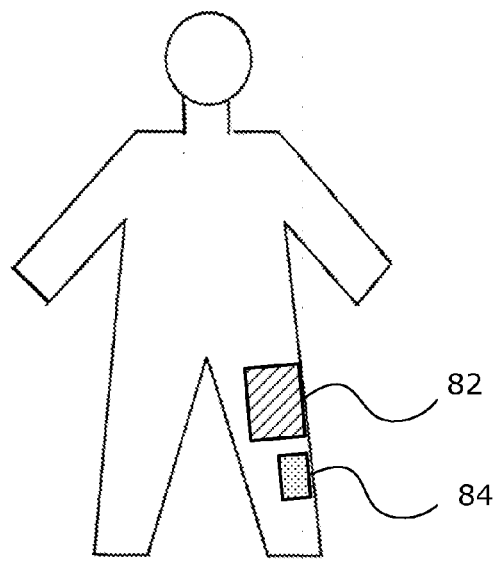
Figure 11D:
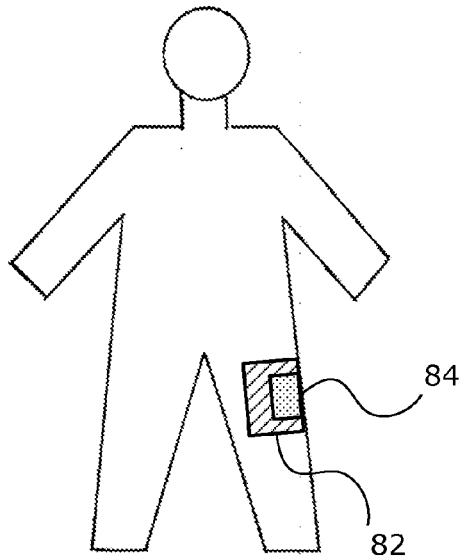

For example, FIGS. 11A-11D show one example of how this binary searching algorithm can be applied. In this particular example, two electrodes have been implanted in the patient's spine, and the tool has determined the functional midline between the two electrodes in the manner described above. The tool receives the location of where the patient is experiencing pain; in this particular case, the left thigh. As shown in FIG. 11A, an area 82 of the left thigh is shown on the display screen as the area where the patient is experiencing pain. With the pain being located on the left side, one or more of the electrode neuromodulation settings are configured to apply neuromodulation to the left side of the spinal cord based on the functional midline of the two electrodes. The patient then indicates where the neuromodulation-induced parasthesia is being felt. In this instance, the patient indicates that the parasthesia is felt on the left abdomen, which is shown as parasthesia area 84 in FIG. 11B. Because the parasthesia area 84 is too high above the targeted pain area 82, the electrode neuromodulation settings are adjusted to direct neuromodulation to an area lower on the spinal cord. After this adjustment, the patient again indicates where the neuromodulation-induced parasthesia is being felt. In this instance, as shown in FIG. 11C, the patient indicates that the parasthesia area 84 is being felt on the left calf below the pain area 82. As shown in FIG. 11D, with further adjustments to the neuromodulation settings, the area of parasthesia 84 is now within the area of pain 82. Since this area of parasthesia 84 is not sufficient to cover the entire area of pain 82, the pulse intensity may need to be increased to achieve sufficient reduction in pain.

Electrode Migration

One of the problems associated with spinal cord neuromodulation is changes in the position of the electrode after its implantation. For example, the electrode may migrate to a different location (e.g., move downwards or move to the side in a "windshield-wiper" fashion) or change its orientation (e.g., the long axis of the electrode may tilt to a different direction, or in the case of a directional electrode contact, rotate towards a different direction). This change in the position of the electrode can result in a loss of therapeutic efficacy. In certain embodiments, the tool of the present invention can adjust the neuromodulation settings to accommodate for the change in electrode position. A change in the position of the electrode can be detected on a radiologic image, such as x-ray images, in the manner described above.

In some cases, the tool may compare the position of the electrode in a radiologic image taken prior to migration of the electrode (e.g., a post-operative x-ray) to the position of the electrode after migration. Based on the relative positioning of the electrode before and after migration, the tool can adjust one or more of the electrode neuromodulation settings to redirect the neuromodulation to the original target. In the example shown in FIG. 12A, an electrode comprising a lead body 96 and three electrodes 93, 94, and 95 are shown prior to migration. At this position, electrode contact 95 is activated to produce a volume of activation 97 that is directed to target site 92 on spinal cord 90.

Figure 12A:
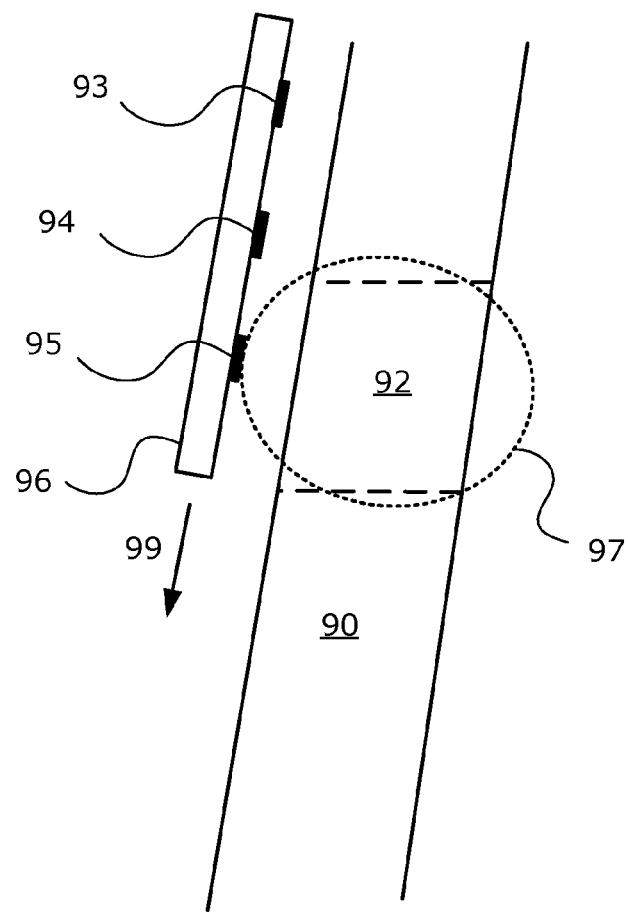
FIGS. 12A and 12B demonstrate an example of how the neuromodulation settings can be adjusted to accommodate for a change in electrode position.
Figure 12B:
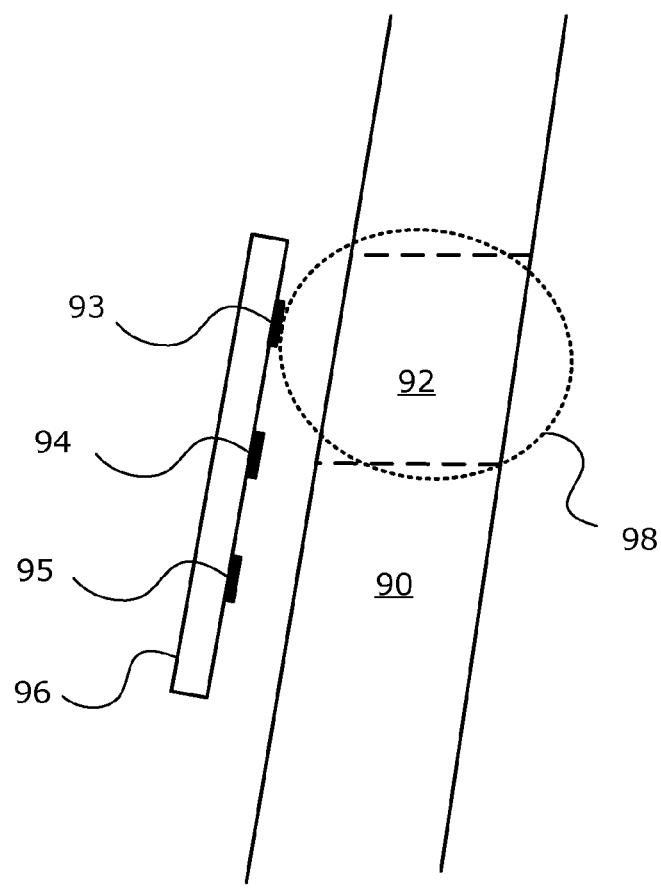
Figure 13:
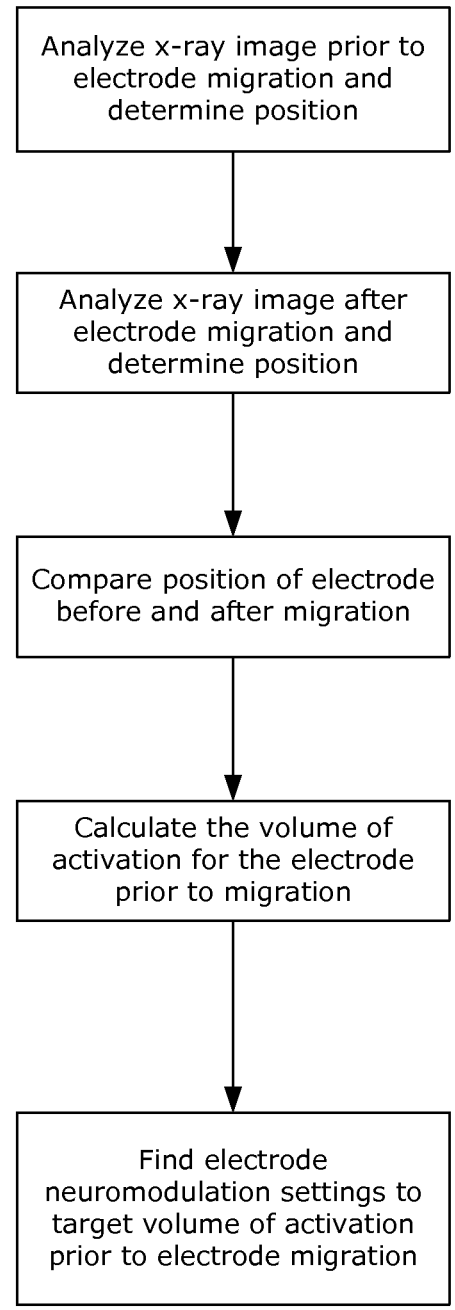
FIG. 13 shows a flowchart illustrating an example of how the neuromodulation settings can be adjusted to accommodate for a change in electrode position.

FIG. 12B shows the same electrode after downward migration along spinal cord 90 (see arrow 99 in FIG. 12A). Because of this migration, the prior neuromodulation settings are ineffective because the electrode has shifted relative to target site 92. But by comparing the relative position of the electrode before and after migration, the electrical neuromodulation settings may be adjusted to redirect the electrical neuromodulation to the original target site 92. Using the targeting methods described above, the tool finds a set of neuromodulation settings with the selection of electrode contact 93 that creates a volume of activation 98 that overlaps with target site 92 or volume of activation 97. As a result, the tool has accommodated the electrical neuromodulation for electrode migration. FIG. 13 shows a flowchart illustration of the above process. Positional changes in the electrodes can also be determined from means other than by radiologic imaging. For example, the electrode may have an accelerometer that detects the position of the electrode. The tool may determine positional changes in the electrode based on the information from the accelerometer.

Thus, in certain embodiments, the tool receives a first radiologic image of an electrode inside a patient, wherein the electrode is in a first position. The tool further receives a second radiologic image of the electrode after a change in the electrode's position, wherein the electrode is in a second position. The tool determines the position of the electrode in the second position relative to the electrode in the first position and calculates a first volume of activation generated by the electrode in the first position. The tool can then determine an electrode neuromodulation setting for the electrode in the second position that produces a second volume of activation that at least partially encompasses the first volume of activation. The tool may display the second volume of activation on a display screen.

In some cases, the tool calculates multiple test volumes of activation using different electrode neuromodulation settings and compares the multiple test volumes of activation to the first volume of activation. Based on the comparison of the multiple test volumes of activation, the tool selects an electrode neuromodulation setting for the electrode in the second position that produces the second volume of activation.

Automated Serial Review of Electrode Contacts

In certain embodiments, the tool may also have a programming mode that automates the standard monopolar review process. In this mode, the user is asked to identify the pain location and severity. Then, each consecutive electrode contact is activated at a tolerable amplitude. The patient is asked to identify the location of the parasthesia and what level of pain they are currently feeling. This is repeated for each available electrode contact. Once each contact has been tested, the user may be given the option of having the tool interpolate the mapped data to predict the best neuromodulation settings. SFMs may be computed and displayed for each successive activation and displayed in real-time to the user, together with real-time display of the parasthesia locations on a three-dimensional model. Real-time display of SFMs and parasthesia locations may also be performed in other programming modes (e.g., the manual programming mode described below in connection with the interface features).

Software and Machine Embodiments

The tool of the present invention may also be embodied as a computer-readable storage medium having executable instructions for performing the various processes as described herein. The storage medium may be any type of computer-readable medium (i.e., one capable of being read by a computer), including non-transitory storage mediums such as magnetic or optical tape or disks (e.g., hard disk or CD-ROM), solid state volatile or non-volatile memory, including random access memory (RAM), read-only memory (ROM), electronically programmable memory (EPROM or EEPROM), or flash memory. The term "non-transitory computer-readable storage medium" encompasses all computer-readable storage media, with the sole exception being a transitory, propagating signal.

The tool of the present invention may also be embodied as a computer system that is programmed to perform the various processes described herein. The computer system may include various components for performing these processes, including processors, memory, input devices, and/or displays. The computer system may be any suitable computing device, including general purpose computers, embedded computer systems, network devices, or mobile devices, such as handheld computers, laptop computers, notebook computers, tablet computers, and the like. The computer system may be a standalone computer or may operate in a networked environment.

Interface Features

The tool may use any of a variety of interface features for interacting with a user. These interactions may include receiving inputs, producing outputs, displaying information, storing program settings, making selections (e.g., target sites, neuromodulation settings, etc.), and the like. The interface features may be adapted for any of the various potential users of the tool, including clinicians, care providers, technicians, salespeople, or the patients themselves. The interface may be provided through any suitable hardware devices, including touch screens, touch pads, mouse, trackball, buttons, wheels, dials, etc. For example, the tool may display a three-dimensional human figure the user may be able point to and select a part of the human figure by a touch screen or a mouse. Various types of interface features which may be used by the tool include those described in U.S. Patent Application Publication No. 2009/0287271 (Blum et al.), which is incorporated by reference herein. The tool may display on a display screen any of the elements described above, including the volumes of activation, spinal anatomy (e.g., of the vertebrae, spinal cord, or both), radiologic images, electrodes, human figures, and such, either individually or in combination.

The tool may also have a manual programming mode in which previously trialed neuromodulation settings are displayed. Another feature may allow the user to customize a neuromodulation region, and then drag the region to the area of the spinal cord for trial simulations of neuromodulation; or allow the user to attempt neuromodulation settings believed to be advantageous by offering a specific visual history of previously attempted settings. The recorded results of the previously attempted settings may be displayed in two or three-dimensional space. For example, the patient's pain zone can be displayed on a three-dimensional model together with the parasthesia zones that resulted from a set of attempted settings. The three-dimensional model may be displayed in conjunction with the display of SFMs calculated for the set of attempted settings (e.g., in a separate display area that shows a three-dimensional model of the spinal cord). The patient's pain zone can be mapped on the human figure and distinguished in some way (by color, for example). The previous parasthesia zones from trial simulations can appear on the human figure. These zones may directly show a result, such as efficacy or indication of pain, by a different color or shade, or they may have text that appears inside them or in a pop-up when the user hovers or clicks the computer's pointing mechanism over the region. Example text may include Visual Analogue Scale (VAS) scores and stimulation settings. The corresponding volume of activation shown on the spinal cord could also be highlighted or identified when the user selects the affected dermatome. This feature would allow the user to easily see which dermatomes are impacted by the neuromodulation zones, and vice versa.

After viewing the results the user may wish to trial a volume of activation that has not been previously trialed. The manual programming mode in the tool can feature a simple method to trial an area of the spinal cord by entering a mode that displays a desired volume of activation that can be manipulated by the user. Alternatively, the user could start with a previously trialed volume of activation. The desired volume of activation may be resized and dragged to the desired location on the spinal cord image. An algorithm would then calculate the closest actual neuromodulation settings that would best fit the zone desired for neuromodulation (i.e., adjusting the settings associated with the previously trialed volume of activation to levels that are appropriate for the resized/re-located volume) and show the user the new settings, who would confirm and trial the neuromodulation. The calculation of the new settings may be performed in a similar fashion to the method previously described for adjusting settings in response to unintended electrode migration, i.e., creating a volume of activation that overlaps with the new volume. The algorithm may take into consideration factors pertaining to the new location, such as CSF thickness, when calculating the new settings. Since it may be advantageous to view the depth of tissue affected by the neuromodulation, a slidable bar can be featured along the side of the posterior spinal cord view. The bar may be positioned to the precise location that a cross-sectional view is desired. In the cross-sectional view, the slidable bar could be used to sequentially browse through different cross-sectional views. Once positioned, the bar is selected or clicked to bring a cross-sectional view that displays the desired volumes of activation as well as offers the same feature of using a desired volume of activation that can be manipulated by the user.

Once results of the manual programming mode are optimized, the final settings may be saved to memory, named, and the user is returned to the main programming page. Saved settings may be selected and displayed via an interface menu. Settings may be merged to combine a plurality of saved settings into a single set of saved settings. For example, settings targeting different pain zones may be combined in order to provide a custom course of treatment for a patient experiencing pain in more than one zone. Similarly, settings that by themselves fail to provide adequate pain zone coverage may be combined to provide sufficient coverage.

The foregoing description and examples have been set forth merely to illustrate the invention and are not intended as being limiting. Each of the disclosed aspects and embodiments of the present invention may be considered individually or in combination with other aspects, embodiments, and variations of the invention. Further, while certain features of embodiments of the present invention may be shown in only certain figures, such features can be incorporated into other embodiments shown in other figures while remaining within the scope of the present invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

What is claimed is:

1. A computer-implemented method for assisting planning or performing of neuromodulation in a patient, comprising:
   storing, by a computer processor, a mapping of each of a plurality of anatomical neuromodulation candidate regions to respective stimulation effect regions that are different than the plurality of anatomical neuromodulation candidate regions;
   receiving, by the processor, input by which one of the stimulation effect regions is selected;
   responsive to the input, determining, by the processor, one or more electrode neuromodulation settings estimated by the processor to produce a volume of tissue activation that at least partially encompasses a target anatomical neuromodulation candidate region, of the plurality of anatomical candidate regions, which is mapped in the stored mapping to the selected one of the plurality of stimulation effect regions; and
   outputting, by the processor, at least one of the one or more electrode neuromodulation settings and a display of the estimated volume of tissue activation.

2. The method of claim 1, further comprising:
   storing, by the processor, a position of one or more electrodes relative to the plurality of anatomical neuromodulation candidate regions; and
   determining, by the processor and based on the stored position, one or more electric fields producible by the one or more electrodes relative to the plurality of anatomical neuromodulation candidate regions, wherein the estimation of the production of the volume of tissue activation for at least partially encompassing the target anatomical neuromodulation candidate region is based on the determined one or more electric fields.

3. The method of claim 1, further comprising:
obtaining, by the processor, a functional image of the patient's anatomy, wherein the functional image includes a representation of the one or more electrodes and a graphical representation of the plurality of anatomical neuromodulation candidate regions; and
registering the position of the one or more electrodes relative to the plurality of anatomical neuromodulation candidate regions based on the functional image.

4. The method of claim 3, wherein the functional image is of the vertebral column.

5. The method of claim 4, wherein the location of the vertebral bodies of the vertebral column is registered in the functional image.

6. The method of claim 5, wherein the functional image includes information that associates one or more of the vertebral bodies in the functional image with a dermatome.

7. The method of claim 3, wherein the functional image includes an x-ray image of the patient's spine.

8. The method of claim 1, wherein the plurality of anatomical neuromodulation candidate regions are of the spinal anatomy and the stimulation effect regions are dermatomes.

9. The method of claim 8, wherein:
the input is a selection of a location on the patient's body; and
responsive to the input:
the processor associates the location with one of the dermatomes; and
uses the mapping to map the associated dermatome to the target anatomical neuromodulation candidate region.

10. The method of claim 7, wherein the location on the patient's body is received as a sensory signal from a sensory nerve.

11. The method of claim 1, further comprising displaying the target anatomical neuromodulation candidate region on the display screen.

12. The method of claim 1, wherein the input identifies a dermatome on the patient's body, and the processor responsively determines, based on the mapping and as the target anatomical neuromodulation candidate region, the anatomical neuromodulation candidate region that is associated with the identified dermatome.

13. The method of claim 1, further comprising fine-tuning the one or more electrode neuromodulation settings based on a received electromyographic signal indicating a location of parasthesia being sensed by the patient.

14. The method of claim 1, further comprising:
receiving a radiologic image of the patient showing one or more electrodes inside the patient;
locating the one or more electrodes in the radiologic image, wherein the one or more electrodes collectively include multiple electrode contacts;
determining a functional midline for the one or more electrodes; and
displaying on a display screen, an image of (a) an anatomic region that encompasses the plurality of anatomical neuromodulation candidate regions and (b) the one or more electrodes such that the functional midline of the one or more electrodes is aligned to the physiologic midline of the anatomic region.

15. The method of claim 14, wherein the step of determining the functional midline comprises:
receiving information about the relative electrical neuromodulation intensity between a first electrode contact among the multiple electrode contacts and a first counterpart electrode contact among the multiple electrode contacts; and
based on the relative electrical neuromodulation intensities, determining a first midpoint between the first electrode contact and the first counterpart electrode contact.

16. The method of claim 15, wherein the step of determining the functional midline further comprises:
receiving information about the relative electrical neuromodulation intensity between a second electrode contact among the multiple electrode contacts and a second counterpart electrode contact among the multiple electrode contacts;
based on the relative electrical neuromodulation intensities, determining a second midpoint between the second electrode contact and the second counterpart electrode contact; and
establishing the functional midline as a line between the first midpoint and the second midpoint.

17. The method of claim 15, wherein multiple electrodes are located in the radiologic image; and wherein the first electrode contact is on a first one of the multiple electrodes and the first counterpart electrode contact is on a second one of the multiple electrodes.

18. The method of claim 17, wherein the step of determining the functional midline further comprises:
receiving information about the relative electrical neuromodulation intensity between a second electrode contact on the first one of the multiple electrodes and a second counterpart electrode contact on the second one of the multiple electrodes;
based on the relative electrical neuromodulation intensities, determining a second midpoint between the second electrode contact and the second counterpart electrode contact; and
establishing the functional midline as a line between the first midpoint and the second midpoint.

19. The method of claim 17, further comprising determining the relative position of the multiple electrodes in relation to each other.

20. The method of claim 15, wherein the relative electrical neuromodulation intensity between the first electrode contact and the first counterpart electrode contact is an electrode neuromodulation setting that produces a parasthesia that is centered on the patient's body.

21. The method of claim 1, further comprising:
receiving a first radiologic image showing an electrode and an anatomic region of the patient that encompasses the plurality of anatomical neuromodulation candidate regions;
receiving a second radiologic image showing the electrode and the anatomic region of the patient, wherein the second radiologic image provides a different view than the first radiologic image; and
using the first radiologic image and the second radiologic image to determine the three-dimensional position of the electrode in relation to the anatomic region, wherein the estimation of the volume of tissue activation relative to the target anatomical neuromodulation candidate region is based on the determined three-dimensional position of the electrode.

22. The method of claim 21, wherein the first radiologic image and second radiologic image show multiple electrodes, and further comprising:
using the first radiologic image and the second radiologic image to determine the three-dimensional position of the multiple electrodes in relation to each other.

23. The method of claim 21, wherein the first radiologic image and second radiologic image are x-ray images.

24. The method of claim 23, wherein the first radiologic image is an anterior-posterior view x-ray image and the second radiologic image is a lateral view x-ray image.

25. The method of claim 1, wherein the neuromodulation is spinal cord neuromodulation, and the functional regions are of the patient's spinal anatomy.

26. The method of claim 1, further comprising:
receiving information about the relative electrical neuromodulation intensity between a first electrode contact of a first electrode and a first counterpart electrode contact of a second electrode;
based on the relative electrical neuromodulation intensities, determining a first midpoint between the first electrode contact and the first counterpart electrode contact;
receiving information about the relative electrical neuromodulation intensity between a second electrode contact of the first electrode and a second counterpart electrode contact of the second electrode;
based on the relative electrical neuromodulation intensities, determining a second midpoint between the second electrode contact and the second counterpart electrode contact;
establishing a functional midline as a line between the first midpoint and the second midpoint;
wherein the input includes user input indicating a side of the patient's spinal cord, and the determination of the one or more neuromodulation settings is of settings estimated by the processor to produce the volume of activation at a side of the functional midline that corresponds to the side of the patient's spinal cord indicated by the received user input.

27. The method of claim 1, further comprising:
outputting a user interface display of an anatomical atlas, wherein the input is user user input, the user input being performed by user selection of a location in the displayed anatomical atlas.

28. A computer system comprising:
a computer processor that is programmed to perform steps that comprise:
providing a functional image of the patient's anatomy, wherein the functional image of the anatomy includes an electrode and information defining functional regions of the anatomy according to one or more neurologic functions;
determining the position of the electrode relative to the functional regions;
based on the one or more neurologic functions, selecting one of the defined functional regions as a target functional region of the anatomy;
providing an electric field model of the electrode based on its determined relative position; and
determining, based on the electric field model, one or more electrode neuromodulation settings that produces a volume of activation that is estimated to at least partially encompass the targeted functional region of the anatomy.

29. The computer system of claim 28, further comprising:
receiving a first radiologic image showing the electrode and an anatomic region of the patient that encompasses the functional regions;
receiving a second radiologic image showing the electrode and the anatomic region of the patient, wherein the second radiologic image provides a different view than the first radiologic image; and
using the first radiologic image and the second radiologic image to determine the three-dimensional position of the electrode in relation to the anatomic region, wherein the volume of activation is estimated by the system based on the determined three-dimensional position.

30. The system of claim 28, wherein the functional image is of the patient's spinal anatomy and includes information defining functional regions of the spinal anatomy.

31. A non-transitory computer-readable storage medium comprising instructions executable by a computer processor, the instructions which, when executed by the processor, cause the processor to perform a method, the method comprising:
providing a functional image of the patient's anatomy, wherein the functional image of the anatomy includes one or more electrodes and information defining functional regions of the anatomy according to one or more neurologic functions;
determining the position of the one or more electrodes relative to the functional regions;
based on the one or more neurologic functions, selecting one of the defined functional regions as a target functional region of the anatomy;
providing an electric field model of the one or more electrodes based on its determined relative position; and
determining, based on the electric field model, one or more electrode neuromodulation settings that produces a volume of activation that is estimated to at least partially encompass the targeted functional region of the anatomy.

32. The non-transitory computer-readable storage medium of claim 31, further comprising:
locating the one or more electrodes in the radiologic image, wherein the one or more electrodes collectively include multiple electrode contacts; and
determining a functional midline for the one or more electrodes.

33. The non-transitory computer-readable storage medium of claim 31, wherein the method further comprises:
receiving a first radiologic image showing the electrode and an anatomic region of the patient that encompasses the functional regions;
receiving a second radiologic image showing the electrode and the anatomic region of the patient, wherein the second radiologic image provides a different view than the first radiologic image; and
using the first radiologic image and the second radiologic image to determine the three-dimensional position of the electrode in relation to the anatomic region, wherein the volume of activation is estimated by the processor based on the determined three-dimensional position.

34. The non-transitory computer-readable storage medium method of claim 33, wherein the anatomic region is a spinal anatomy of the patient.

35. The system of claim 31, wherein the functional image is of the patient's spinal anatomy and includes information defining functional regions of the spinal anatomy.

36. A computer-implemented method for assisting the planning or performing of neuromodulation in a patient, comprising:
receiving, by a computer processor, a first radiologic image of an electrode inside a patient, wherein the electrode is in a first position;
receiving, by the processor, a second radiologic image of the electrode after a change in the position of the electrode, wherein the electrode is in a second position;

determining, by the processor and based on the received first and second images, the position of the electrode in the second position relative to the electrode in the first position;

calculating, by the processor, a first volume of activation estimated to be generated by the electrode in the first position;

determining, by the processor, an electrode neuromodulation setting for the electrode in the second position estimated by the processor to produce a second volume of activation that at least partially encompasses the first volume of activation; and displaying, by the processor, the second volume of activation on a display screen.

37. The method of claim 36, further comprising:
calculating multiple test volumes of activation using different electrode neuromodulation settings;
comparing the multiple test volumes of activation to the first volume of activation; and
based on the comparison of the multiple test volumes of activation, selecting an electrode neuromodulation setting for the electrode in the second position that produces the second volume of activation.

38. The method of claim 37, wherein the step of comparing the multiple test volumes of activation to the first volume of activation includes calculating a score for each test volume of activation, the score comprising the amount of test volume of activation that overlaps with the first volume of activation.

39. The method of claim 36, further comprising displaying the first volume of activation on the display screen.

40. The method of claim 36, wherein the neuromodulation is spinal cord neuromodulation.

41. A computer system that is programmed to perform steps that comprise:
receiving a first radiologic image of one or more electrodes inside a patient, wherein the one or more electrodes is in a first position;
receiving a second radiologic image of the one or more electrodes after a change in the position of at least one of the one or more electrodes, wherein the one or more electrodes is in a second position;
determining the position of the one or more electrodes in the second position relative to the one or more electrodes in the first position;
calculating a first volume of activation generated by the one or more electrodes in the first position; and
determining an electrode neuromodulation setting for the one or more electrodes in the second position that produces a second volume of activation that at least partially encompasses the first volume of activation.

42. The system of claim 41, wherein the one or more electrodes collectively include multiple electrode contacts, and the method further comprises determining a functional midline for the one or more electrodes.

43. A non-transitory computer-readable storage medium comprising instructions executable by a computer processor, the instructions which, when executed by the processor, cause the processor to perform a method, the method comprising:
receiving a first radiologic image of an electrode inside a patient, wherein the electrode is in a first position;
receiving a second radiologic image of the electrode after a change in the position of the electrode, wherein the electrode is in a second position;
determining, based on the received first and second images, the position of the electrode in the second position relative to the electrode in the first position;
calculating a first volume of activation estimated to be generated by the electrode in the first position; and
determining an electrode neuromodulation setting for the electrode in the second position estimated by the processor to produce a second volume of activation that at least partially encompasses the first volume of activation.

44. A computer-implemented method for assisting the planning or performing of spinal cord neuromodulation in a patient, comprising:
determining, by a computer processor, at least one of (a) a thickness of cerebrospinal fluid at a location at which it separates a spinal cord from an electrode positioned adjacent the spinal cord and (b) a depth of the cerebrospinal fluid at which the cerebrospinal fluid separates the spinal cord from the electrode;
calculating, by the computer processor, a volume of activation estimated to be created, under a set of electrode neuromodulation conditions, by the electrode positioned adjacent the spinal cord, wherein:
the calculation is based on an electric field model of the electrode;
the model is based on a characteristic of the cerebrospinal fluid between the electrode and the spinal cord; and
a degree to which the characteristic of the cerebrospinal fluid affects the model used by the processor for calculating the volume of activation varies depending on the determined at least one of the thickness and depth of the cerebrospinal fluid that separates the electrode from the spinal cord; and
displaying the predicted volume of activation on a display screen.

45. The method of claim 44, wherein:
the method includes the step of determining the depth of the cerebrospinal fluid between the electrode and the spinal cord; and
the method further comprises registering the depth of the cerebrospinal fluid in the electric field model.

46. The method of claim 45, wherein:
the step of determining the depth of the cerebrospinal fluid comprises receiving and processing a radiologic image of the patient showing the spinal cord and the electrode;
the method further comprises calculating the thickness of the cerebrospinal fluid between the spinal cord and the electrode based on the determined depth; and
the electric field model is customized to the calculated thickness.

47. The method of claim 46, wherein the radiologic image is an MR image of the patient's spine.

48. The method of claim 46, wherein the calculation of the thickness of the cerebrospinal fluid comprises using information about the position of the electrode.

49. The method of claim 48, wherein the information about the position of the electrode includes the vertebral level where the electrode is positioned and the thickness of the cerebrospinal fluid is approximated by the vertebral level or the vertebrae size where the electrode is positioned.

50. The method of claim 49, wherein:
the radiologic image shows the electrode and the patient's vertebrae; and
the method further includes:
locating the electrode within the radiologic image; and
determining the vertebral level where the electrode is positioned.

51. A computer system that is programmed to perform steps that comprise:
- determining at least one of (a) a thickness of cerebrospinal fluid at a location at which it separates a spinal cord from an electrode positioned adjacent the spinal cord and (b) a depth of the cerebrospinal fluid at which the cerebrospinal fluid separates the spinal cord from the electrode;
- providing an electric field model of the electrode positioned adjacent the spinal cord, wherein the model is based on a characteristic of the cerebrospinal fluid; and
- using the electric field model to calculate a volume of activation estimated to be created by the electrode under a set of electrode neuromodulation conditions, wherein a degree to which the characteristic of the cerebrospinal fluid affects the model used for the calculation of the volume of activation varies depending on the determined at least one of the thickness and depth of the cerebrospinal fluid that separates the electrode from the spinal cord.

52. A non-transitory computer-readable storage medium comprising instructions executable by a computer processor, the instructions which, when executed by the processor, cause the processor to perform a method, the method comprising:
- determining at least one of (a) a thickness of cerebrospinal fluid at a location at which it separates a spinal cord from an electrode positioned adjacent the spinal cord and (b) a depth of the cerebrospinal fluid at which the cerebrospinal fluid separates the spinal cord from the electrode;
- providing an electric field model of the electrode positioned adjacent the spinal cord, wherein the model is based on a characteristic of the cerebrospinal fluid; and
- using the electric field model to calculate a volume of activation estimated to be created by the electrode under a set of electrode neuromodulation conditions, wherein a degree to which the characteristic of the cerebrospinal fluid affects the model used for the calculation of the volume of activation varies depending on the determined at least one of the thickness and depth of the cerebrospinal fluid that separates the electrode from the spinal cord.

* * * * *